United States Patent
George et al.

(10) Patent No.: US 12,156,840 B2
(45) Date of Patent: Dec. 3, 2024

(54) KNEE REPLACEMENT THERAPY UNIT

(71) Applicant: DYNASPLINT SYSTEMS, INC., Severna Park, MD (US)

(72) Inventors: Michael George, Spring, TX (US); George Hepburn, Severna Park, MD (US); Russell Vedeloff, Greensboro, MD (US)

(73) Assignee: DYNASPLINT SYSTEMS, INC., Severna Park, MD (US)

( * ) Notice: Subject to any disclaimer, the term of this patent is extended or adjusted under 35 U.S.C. 154(b) by 1148 days.

(21) Appl. No.: 16/961,448

(22) PCT Filed: Jan. 15, 2019

(86) PCT No.: PCT/US2019/013693
§ 371 (c)(1),
(2) Date: Jul. 10, 2020

(87) PCT Pub. No.: WO2019/140454
PCT Pub. Date: Jul. 18, 2019

(65) Prior Publication Data
US 2021/0077334 A1 Mar. 18, 2021

Related U.S. Application Data

(60) Provisional application No. 62/616,738, filed on Jan. 12, 2018.

(51) Int. Cl.
*A61H 1/02* (2006.01)
*A61F 2/38* (2006.01)

(52) U.S. Cl.
CPC ............... *A61H 1/024* (2013.01); *A61F 2/38* (2013.01); *A61H 2201/0149* (2013.01);
(Continued)

(58) Field of Classification Search
CPC ................. A61H 1/024; A61H 1/0237; A61H 2201/0149; A61H 2201/1253;
(Continued)

(56) References Cited

U.S. PATENT DOCUMENTS 2,644,447 A * 7/1953 Sanders .................. 601/101
3,009,460 A * 11/1961 Leach ................ A61H 23/0263
601/63

(Continued)

FOREIGN PATENT DOCUMENTS

FR 2995781 A1 3/2014

OTHER PUBLICATIONS

Myaid, "Ortho-Glide Knee Exerciser /Slider, A Knee Rehab Device for Rehabilitation Post Knee Replacements and Surgery," Amazon.co.uk: Health & Personal Care, Amazon.com, Inc., Sep. 27, 2017, Figures and bottom paragraph, www.amazon.co.uk/Ortho-Glide-Exerciser-Rehabilitation-Replacements-Surgery/dp/B00EUXLGZQ.

(Continued)

*Primary Examiner* — Michael R Reid
*Assistant Examiner* — Tyler A Raubenstraw
(74) *Attorney, Agent, or Firm* — Studebaker & Brackett PC

(57) ABSTRACT

A knee replacement therapy unit comprising a base board configured to be attached with a chair; a winch having a crank, the winch attached to the base board and configured to wind a cable thereon; and a feed mechanism attached to the base board and configured to receive a cable therethrough from the winch.

16 Claims, 5 Drawing Sheets

(52) U.S. Cl.
CPC ............... *A61H 2201/0157* (2013.01); *A61H 2201/1253* (2013.01); *A61H 2201/1481* (2013.01); *A61H 2201/1642* (2013.01); *A61H 2203/0431* (2013.01)

(58) Field of Classification Search
CPC .... A61H 2201/1481; A61H 2201/1642; A61H 2203/0431; A61H 1/00; A61H 2230/855; A61H 2201/0431; A61F 2/38
See application file for complete search history.

(56) References Cited

U.S. PATENT DOCUMENTS

| | | | | |
|---|---|---|---|---|
| 3,661,149 | A * | 5/1972 | Ferries | A61H 1/0237 601/35 |
| 3,667,453 | A * | 6/1972 | Schenck | A61H 1/0292 601/87 |
| 3,736,920 | A * | 6/1973 | Mathers | A61H 15/0078 601/99 |
| 4,843,661 | A * | 7/1989 | Skibinski | A61G 7/1038 5/81.1 HS |
| 4,860,733 | A * | 8/1989 | Parker, Jr. | A61H 1/0292 601/24 |
| 4,947,835 | A * | 8/1990 | Hepburn | A61B 17/62 606/56 |
| 5,040,522 | A * | 8/1991 | Daniels | A61H 1/024 601/24 |
| 5,324,245 | A * | 6/1994 | Fontana | A61H 1/024 482/142 |
| 5,333,333 | A * | 8/1994 | Mah | A61H 3/04 280/30 |
| 5,558,624 | A * | 9/1996 | Hepburn | A63B 21/4017 482/136 |
| 5,645,521 | A * | 7/1997 | Hepburn | A63B 21/4045 482/136 |
| 5,725,275 | A * | 3/1998 | Wigfall | A61G 5/1002 297/183.1 |
| 6,342,042 | B1 * | 1/2002 | Martin | A61H 1/0237 601/84 |
| 6,766,543 | B1 * | 7/2004 | Hollis | A47K 3/006 4/578.1 |
| 6,770,043 | B1 * | 8/2004 | Kahn | A61H 9/0071 601/169 |
| 6,908,475 | B2 * | 6/2005 | Hepburn | A61F 5/0118 601/134 |
| 6,942,629 | B2 * | 9/2005 | Hepburn | A61F 5/0125 602/26 |
| 9,427,371 | B1 * | 8/2016 | Lamar | A47C 1/032 |
| 9,782,321 | B1 * | 10/2017 | Semmens | A61N 1/0452 |
| 11,406,867 | B1 * | 8/2022 | Beck | A63B 21/002 |
| 2008/0000317 | A1 * | 1/2008 | Patton | F16H 19/06 623/32 |
| 2008/0249438 | A1 * | 10/2008 | Agrawal | A61H 1/0237 602/23 |
| 2009/0017995 | A1 * | 1/2009 | Freiberg | A63B 21/00181 482/91 |
| 2012/0078142 | A1 * | 3/2012 | Fenkell | A61H 1/024 601/5 |
| 2013/0045843 | A1 | 2/2013 | Eddy | |
| 2013/0320640 | A1 * | 12/2013 | Liu | A61H 3/04 280/42 |
| 2014/0039360 | A1 * | 2/2014 | Spade | A61H 1/024 601/33 |
| 2014/0088466 | A1 | 3/2014 | Hansen | |
| 2014/0094721 | A1 * | 4/2014 | Diallo | A63B 24/0087 601/5 |
| 2015/0351990 | A1 * | 12/2015 | Ewing | A61H 1/0244 601/5 |
| 2016/0236030 | A1 * | 8/2016 | Hsieh | A63B 21/4027 |
| 2017/0035639 | A1 * | 2/2017 | Thomas | A61H 1/0237 |
| 2017/0128775 | A1 | 5/2017 | Santos et al. | |
| 2017/0224571 | A1 * | 8/2017 | Pisano | B62M 1/12 |
| 2017/0239119 | A1 * | 8/2017 | Stewart | A61G 13/1245 |
| 2017/0266476 | A1 * | 9/2017 | Marti | A61B 5/1114 |
| 2017/0340503 | A1 * | 11/2017 | Turner | A61H 1/024 |
| 2017/0348170 | A1 * | 12/2017 | Keepers | A61H 1/0244 |
| 2018/0098905 | A1 * | 4/2018 | Nelson | A63B 23/0494 |
| 2018/0104130 | A1 * | 4/2018 | Sampson | A61H 1/024 |
| 2018/0207049 | A1 * | 7/2018 | Janzen | A61F 5/0585 |
| 2018/0235826 | A1 * | 8/2018 | Jaeger | A61H 1/008 |
| 2018/0311526 | A1 * | 11/2018 | Eddy | A63B 23/0405 |
| 2019/0054342 | A1 * | 2/2019 | Christy | A63B 69/0028 |
| 2019/0111299 | A1 * | 4/2019 | Radcliffe | A61H 1/0274 |
| 2019/0133864 | A1 * | 5/2019 | Cook | A61H 1/024 |
| 2019/0133865 | A1 * | 5/2019 | Almendarez | A61H 1/00 |
| 2019/0168069 | A1 * | 6/2019 | Chizhov | A61H 1/0237 |
| 2020/0046593 | A1 * | 2/2020 | Tsukasako | A61H 1/024 |
| 2020/0093674 | A1 * | 3/2020 | Ewing | A61H 1/0244 |
| 2020/0315899 | A1 * | 10/2020 | Takahashi | B25J 11/00 |
| 2020/0375833 | A1 * | 12/2020 | Patel | A61H 1/0266 |
| 2021/0196551 | A1 * | 7/2021 | Burke | A61H 1/024 |
| 2022/0175604 | A1 * | 6/2022 | Cook | A61H 1/00 |

OTHER PUBLICATIONS

International Search Report issued in corresponding International Application No. PCT/US2019/013693, mailed Apr. 9, 2019, p. 1, U.S. Patent and Trademark Office, Alexandria, VA.

* cited by examiner

KNEE REPLACEMENT THERAPY UNIT

PRIORITY CLAIM AND CROSS-REFERENCE

The present application is a U.S. National Stage of International Application No. PCT/US2019/013693, filed Jan. 15, 2019, which claims priority from U.S. Provisional Application 62/616,738 filed on Jan. 12, 2018, titled, "Total Knee Replacement Therapy Unit," both of which are incorporated herein by reference in their entirety.

BACKGROUND

After a patient has undergone a knee replacement procedure, physical therapy is used to manipulate the knee and improve mobility of the knee of the patient. The patient often undergoes physical therapy in the form of a physical therapist physically manipulating the leg, and thereby the knee, of the patient.

In other embodiments, patients used manual physical therapy or continuous passive movement (CPM) machines to regain their motion in the early post-operative period. The CPM machine requires the patient to lie supine in a bed and is a bulky, expensive, electrical device that also flexes the hip in combination with knee flexion. A flexinator device has also been used in this scenario but this device takes a large amount of space and also flexes the knee in combination with hip flexion. Hip flexion is not ideal when trying to flex the knee because it allows the leg to raise in the device without actually bending the knee and therefore limiting the benefit. Also, hip flexion may be limited and painful in a patient with knee and hip arthritis which also limits the utility of the flexinator.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
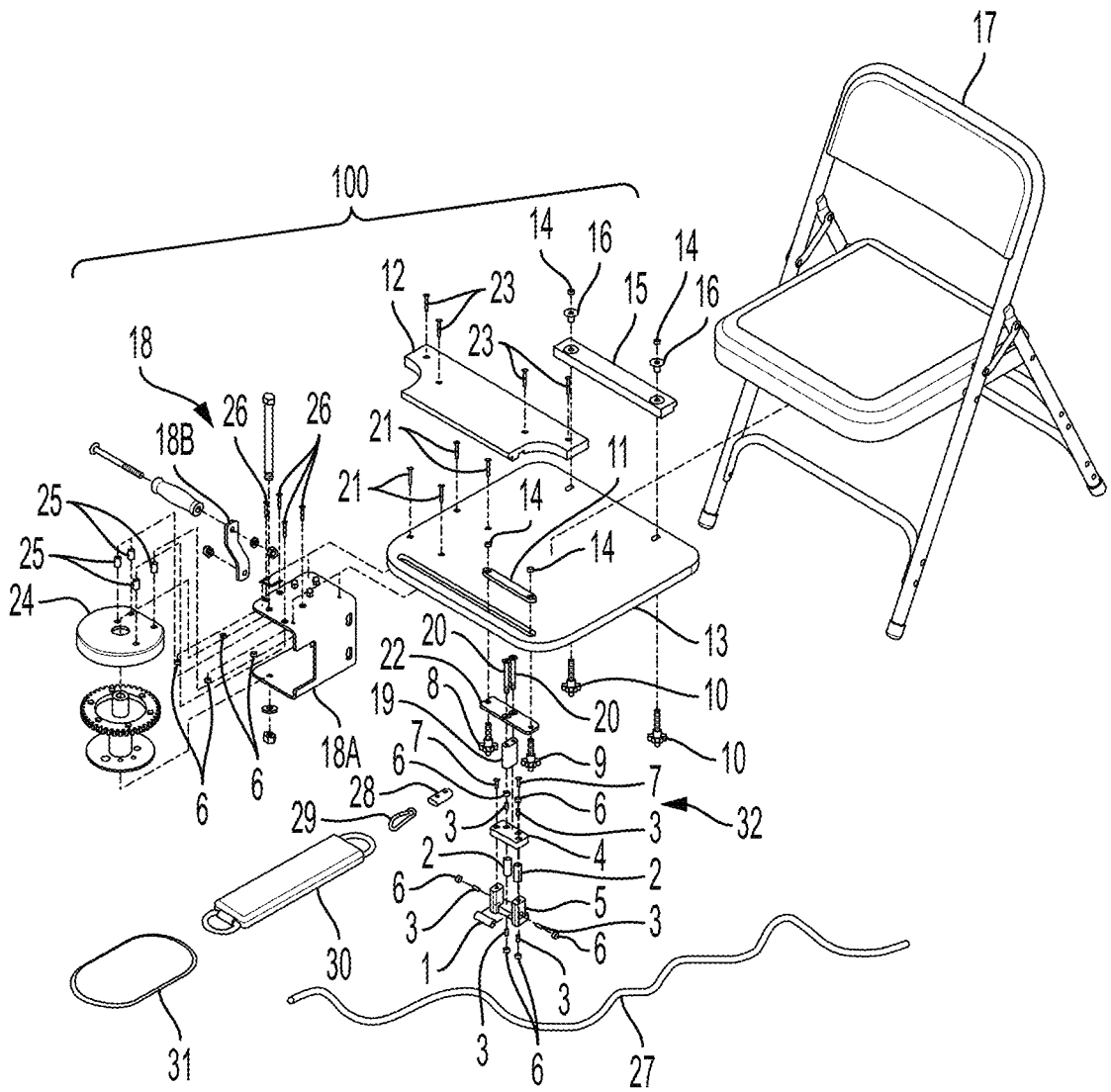
FIG. 1 is an exploded perspective view of a knee replacement therapy unit, in accordance with some embodiments.
Figure 2:
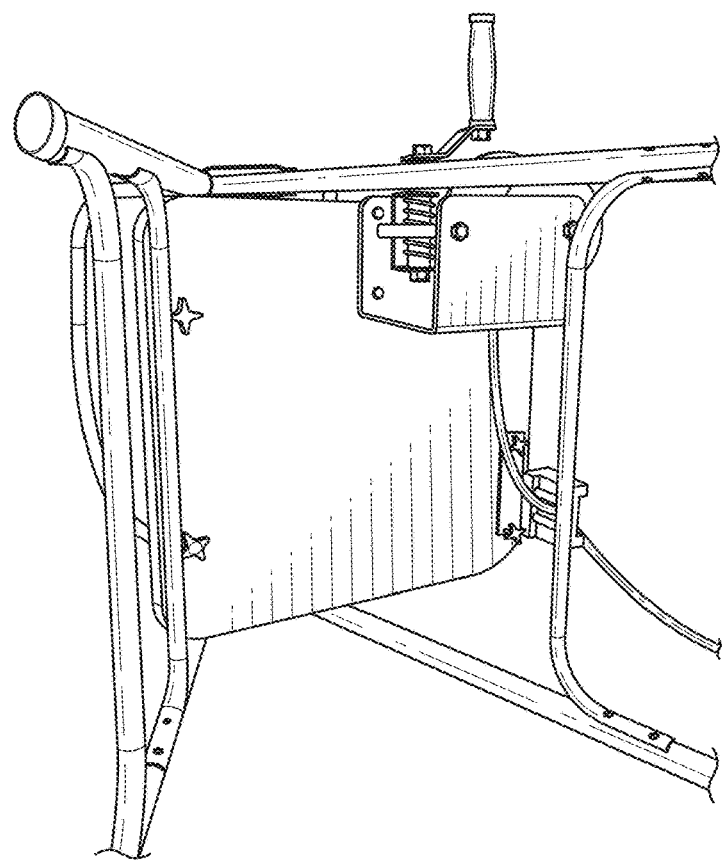
FIG. 2 is a bottom perspective view of the knee replacement therapy unit, in accordance with some embodiments.
Figure 3:
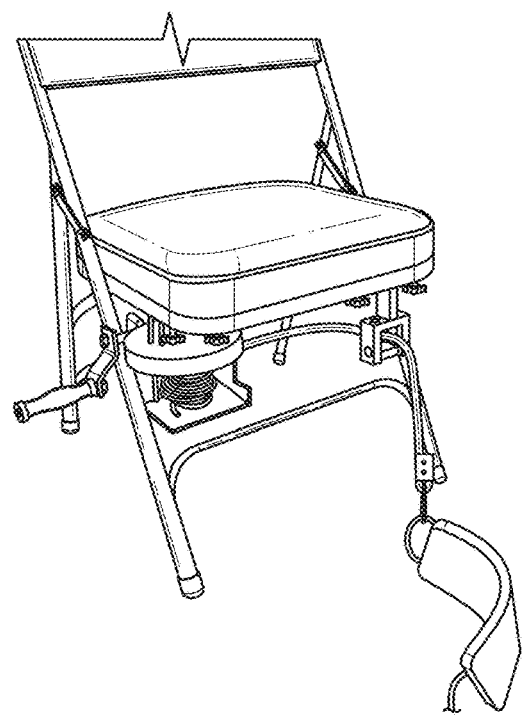
FIG. 3 is a perspective view of the knee replacement therapy unit, in accordance with some embodiments.
Figure 4:
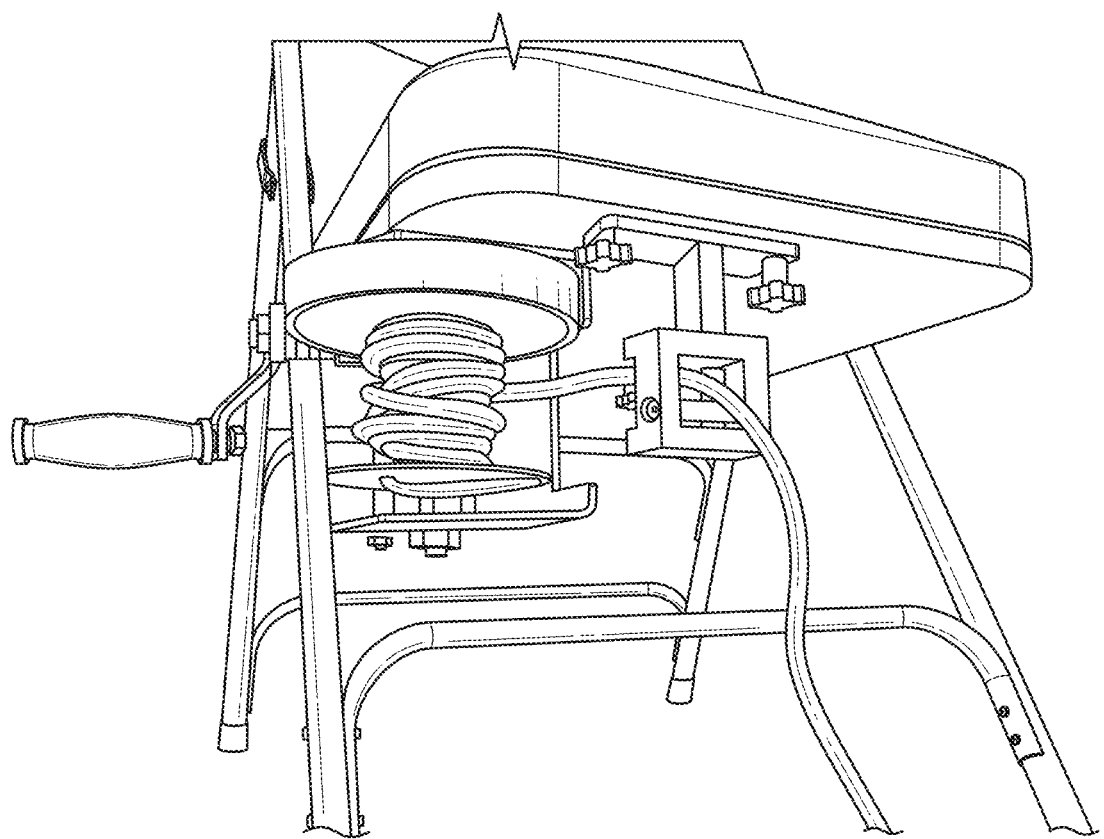
FIG. 4 is another perspective view of the knee replacement therapy unit, in accordance with some embodiments.
Figure 5:
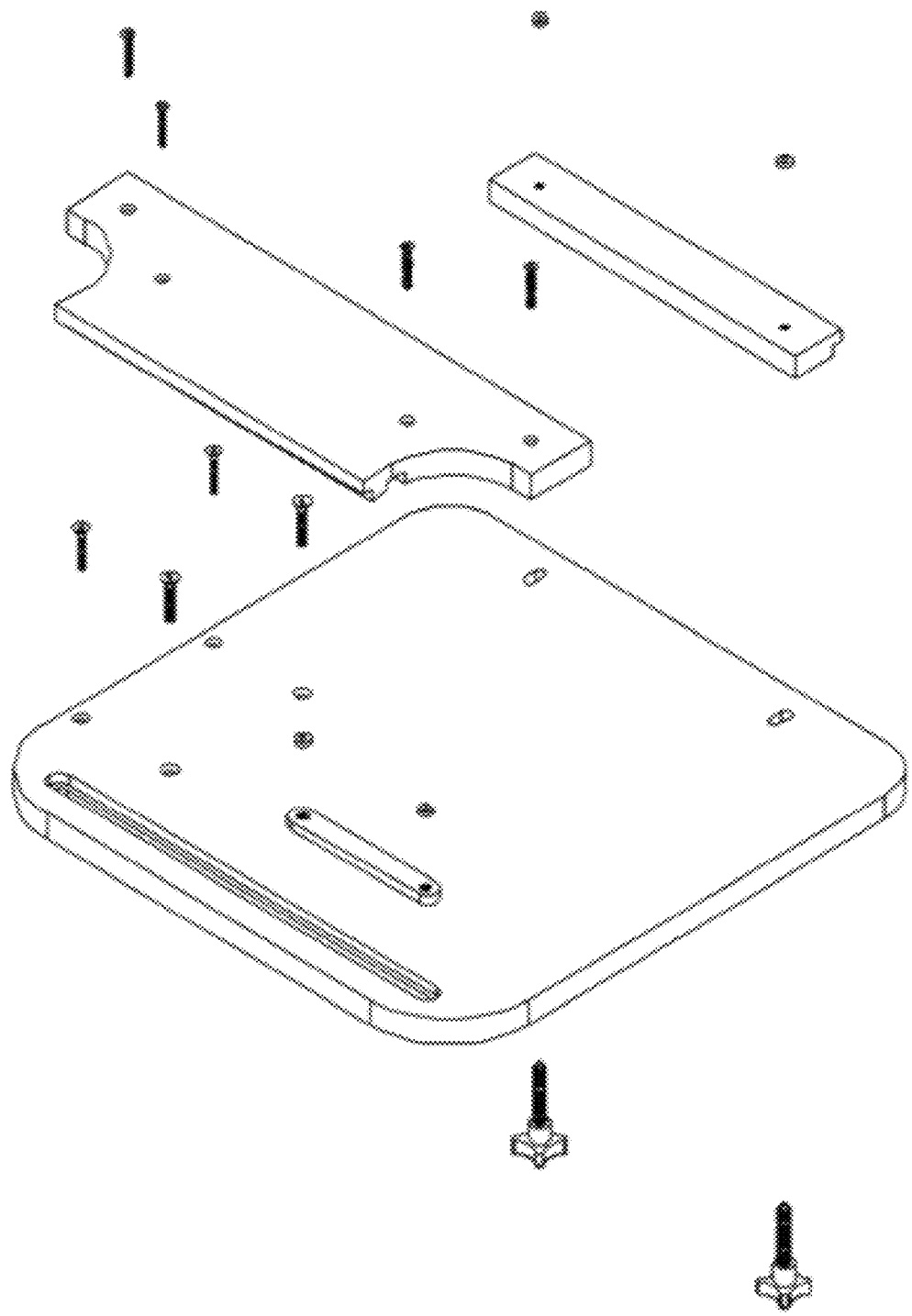
FIG. 5 is an exploded perspective view of a base board, in accordance with some embodiments.
Figure 6:
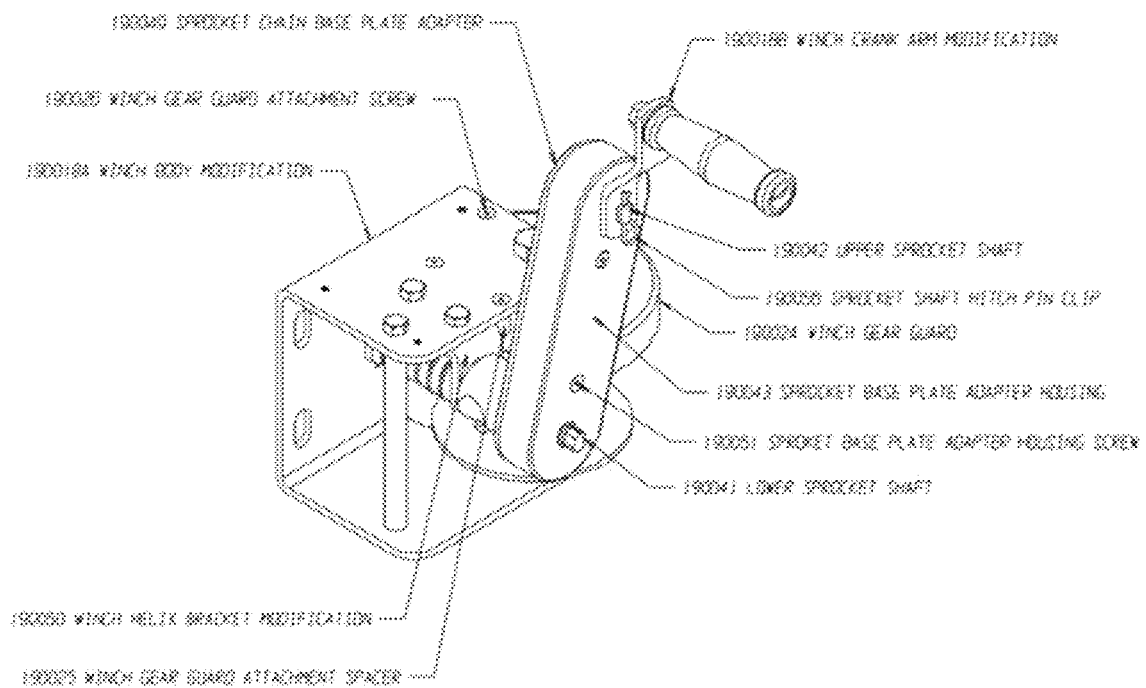
FIG. 6 is a detailed perspective view of a winch, in accordance with some embodiments.

The following disclosure provides many different embodiments, or examples, for implementing different features of the provided subject matter. Specific examples of components, values, operations, materials, arrangements, or the like, are described below to simplify the present disclosure. These are, of course, merely examples and are not intended to be limiting. Other components, values, operations, materials, arrangements, or the like, are contemplated. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" or the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The present disclosure relates to a knee replacement therapy unit 100. The unit 100 is targeted to help those who need knee rehabilitation training to flex their knee joints. In operation, the user sits on a chair 17 to which the unit 100 is attached and positions the foot of the knee to be flexed on a slidable puck on the floor in front of the user with the knee in an unflexed position. A cable is attached to the user's foot. The user is then able to manipulate the therapy unit 100 to cause the cable to be retracted toward the user seated on the chair 17 and thereby cause the knee of the user to flex. The user is able to retract the cable at a rate and to an extent acceptable to the user. For example, due to pain the user may only be able to withstand flexing of the knee to a certain angle or at a certain rate. Thus, the user is in control of the flexure of the user's knee during operation of the unit 100.

In at least some embodiments, the user's leg begins in a substantially straight position with no rotation of the lower leg about the knee pivot point with respect to the upper leg. In at least some embodiments, the user's knee is flexed such that the lower leg forms an angle of from 180 degrees to 90 degrees with respect to the upper leg. In at least some embodiments, the user's knee is flexed to form an angle of from less than 180 degrees to less than 90 degrees. A smaller angle indicates a greater amount of motion of the knee being flexed.

Viewed in another way, during flexion the lower leg is rotated from 0 degrees to 140 degrees from a plane extending from the upper leg. That is, at 0 degrees there is no bending of the leg at the knee and at 90 degrees the upper leg and lower leg form a 90 degree angle.

FIG. 1 is an exploded perspective view of a unit 100, according to an embodiment. The unit 100 comprises a base board 13, a winch 18, a slidable feed mechanism 32, and a slider puck 31. The unit 100 is attachable to an existing chair 17. In accordance with an embodiment, unit 100 is configured to be attached and detached from chair 17. In accordance with an embodiment, unit 100 is configured to be attached and detached from chair 17 without the use of tools and using only the user's hands.

In at least some embodiments, base board 13 is made of plastic, wood, metal, polymer, or the like.

Base board 13 has a rear base board clip plate 15 and a front base board clip plate 12, which are each attached to a same side of the base board. In at least some embodiments, rear base board clip plate 15 is attached to a different side of the base board from front base board clip plate 12. Depending on the configuration of the chair 17 to which the base board is being attached, the front and rear base board clip plates 12/15 are attachable to either the same side (also referred to as a face or a surface) of base board 13 or to different sides of base board 13.

Each of the rear base board clip plate 15 and the front base board clip plate 12 are individually movable with respect to base board 13 in order to secure the base board to chair 17. Base board 13 has an extended opening formed therein and extending parallel along a front edge of the base board for retaining and enabling positioning of the slidable feed mechanism. Base board 13 has another pair of elongated openings formed therein and positioned spaced apart at a rear edge of the base board for retaining and enabling attachment of the unit to chair 17 by way of the rear base board clip plate 12. The elongated openings are each elongated in a direction perpendicular to the rear edge.

The front base board clip plate 12 is attached to the upper surface of base board 13, e.g., via screws, bolts, or similar mechanism. The front base board clip plate 12 has a lip along the front edge extending beyond the body of the clip plate in order to interfit with a portion of chair 17. In some embodiments, the lip and base board 13 form a groove into which an inner projection of chair 17 fits to retain one end of the base board to the chair.

The rear base board clip plate 15 is attached to the upper surface of base board 13 via bolts or other releasable devices extending through the pair of elongated openings formed in the base board. The bolts are able to be tightened/loosened in order to be able to slide rear base board clip plate 15 along base board 13. Similar to front base board clip plate 12, the rear base board clip plate 15 has a lip along the rear edge extending beyond the body of the clip plate in order to interfit with a portion of chair 17. In some embodiments, the lip and base board 13 form a groove into which an inner projection of chair 17 fits to retain one end of the base board to the chair. The elongated openings enable movement of the rear base board clip plate 15 away from/toward the rear edge of the base board. In this manner with the rear base board clip plate 15 positioned toward the interior of the base board, the base board is able to be positioned into the lower portion (underside of the seat pan) of the chair. The lip of the front base board clip plate 12 engages the inner projection of the chair and the body of the base board is rotated into position to bring the rear base board clip plate 15 within the lower portion of the chair. After the base board is in position, the rear base board clip plate 15 is moved toward the rear edge of the base board. The bolts extending through the elongated openings are tightened and the base board, and unit 100, is securely attached to the chair 17.

Base board 13 also includes winch 18 which comprises a winch body opening 18a, a gear mechanism, a handle, and a winch crank arm 18b. Winch 18 is connected along a side edge between the front and rear edges of base board 13. The handle is attached to the winch crank arm 18b, which is connected to a worm gear drive mechanism, and is rotatable by a user to activate/rotate the winch 18. Winch 18 is connected along a right-hand side of base board 13, but in other embodiments is connectable to the left-hand side of the base board. A cable 27 is used in conjunction with the unit 100. One end of cable 27 is connected to the winch and the other end is connectable with a cuff 30. In at least some embodiments, cuff 30 is an ankle cuff for surrounding a user's ankle in use. Winch body opening 18a enables passage of cable 27 from the winch to the slidable feed mechanism and the cuff. When in use, the winch 18 is attached to the base board, e.g., via bolts or other similar mechanism. As a user rotates the handle, the winch 18 extends or retracts cable 27 and the attached cuff at the other end of the cable. In some embodiments, cable 27 is a metal material. In some embodiments, cable 27 is a plastic material. In some embodiments, cable 27 is a polymer material. In some embodiments, cable 27 is high strength cotton rope.

Base board 13 also includes the slidable feed mechanism which comprises a pair of vertically-oriented rollers for redirecting movement of cable 27 to be in line with the user's movement when seated in chair 17. With the user seated in chair 17, the slidable feed mechanism is aligned under the leg of the user to be manipulated and as the winch takes up cable 27 the lower leg, having the cuff attached, is pulled back toward the chair and slidable feed mechanism in a normal flexion of the knee motion. Although winch 18 is offset, the slidable feed mechanism enables cable 27 to move in line with flexion of the knee. The slidable feed mechanism also comprises bolts or other releasable devices extending through the extended opening of base board 13 to retain the slidable feed mechanism to the base board. The bolts are able to be tightened/loosened in order to be able to slide the slidable feed mechanism along base board 13. The extended opening enables movement of the slidable feed mechanism along the front edge of base board 13. The extended opening enables positioning of the slidable feed mechanism from side to side along the front edge of base board 13. Thus, the slidable feed mechanism is positionable under either of a user's left or right thigh.

In at least some embodiments, slidable feed mechanism also comprises a pair of horizontally-oriented rollers for redirecting movement of cable 27 to be in line with the user's movement when seated in chair 17. In at least some embodiments, slidable feed mechanism solely comprises a pair of horizontally-oriented rollers. In at least some embodiments, slidable feed mechanism solely comprises a single vertically- and/or horizontally-oriented roller.

Slider puck 31 is for a user to place the foot or heel of the foot on in order to reduce friction between the foot and the floor. Slider puck 31 is used to more easily move the user knee through flexion with the foot on the floor. Slider puck 31 can slide in any direction and having the slidable feed mechanism aligned with the user's leg enables the leg to flex toward the chair. In some embodiments, slider puck 31 is omitted and the user slides their foot directly on the floor.

In at least some embodiments, slider puck 31 is made of plastic, wood, metal, polymer, or the like. In at least some embodiments, slider puck 31 has a concave upper surface for receiving a portion of a user's foot thereon. In at least some embodiments, at least one side of slider puck 31 is smooth to enable sliding of the puck on a flooring surface. For example, the slider puck 31 has a lower coefficient of friction than the surface on which it is to be used in some embodiments.

One end of the cable 27 is tied to the winch 18, the other end passes through the slidable feed mechanism and is connected to the cuff 30. Moreover, slider puck 31, for the user to place his/her foot on, helps to reduce the friction between the foot and the floor.

When using this unit, the user first attaches base board 13 to the underside of an existing chair using one or both of the front and rear base board clip plates. After sitting on the chair and putting one foot on slider puck 31, the user wraps cuff 30 around the user's ankle. Then, the user rotates the handle to retract the cable 27 to pull back the user's lower leg and flex the knee joint. When the user wants to stretch the leg, the user rotates the handle to extend the cable 27 and leave space for the leg to extend. With the help of this unit, people can more easily exercise their knee joints.

In at least some embodiments, a winch 18 is used having a release mechanism for allowing a release cable to be pulled freely off the winch. In this embodiment, when the user wants to stretch the leg, the user releases the winch allowing cable to be pulled freely off the winch and extends the user's leg.

This total knee replacement therapy unit is user-driven. The unit is light in weight, e.g., less than 30 lbs and small in size, thus easily-portable and/or transportable by a user. The unit is attachable and removable from an existing chair. No extra tools are needed.

While using the unit, the user turns the handle clockwise or counter-clockwise to extend or retract the cable 27. The slidable feed mechanism is slidable through the groove in the base board to the left or right in order to align with the user's left or right thigh. By doing so, this unit can be applied to either knee of a user.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A knee replacement therapy unit, the unit comprising:
a base board configured to be attached with a chair;
a winch having a crank, the winch attached to the base board and configured to wind a cable thereon; and
a feed mechanism attached to the base board and configured to receive a cable therethrough from the winch,
wherein the base board further comprises a front base board clip plate and a rear base board clip plate, each of the front and rear base board clip plates are on a side of the base board and parallel to an edge of the base board, the front and rear base board clip plates are configured to attach the knee replacement therapy unit to the chair, and
at least one of the front or rear base board clip plate in conjunction with the base board forms a groove therebetween having an opening in the same direction as the edge of the base board to which the front or rear base board clip plate is attached.

2. The knee replacement therapy unit of claim 1 wherein the winch is attached on a surface of the base board opposite the front base board clip plate.

3. The knee replacement therapy unit of claim 1 wherein the base board further comprises:
a first base board clip plate on a first side of the base board and parallel to a first edge of the base board; and
a second base board clip plate on a second side of the base board and parallel to a second edge of the base board, and
wherein the first side is opposite the second side.

4. The knee replacement therapy unit of claim 3, wherein the first edge is parallel with the second edge.

5. The knee replacement therapy unit of claim 1 wherein the feed mechanism is slidably attached to the base board in a direction parallel to an edge of the base board.

6. The knee replacement therapy unit of claim 1 wherein the feed mechanism is removably attached to the base board.

7. The knee replacement therapy unit of claim 1 wherein the cable is made of a metal material, a plastic material, a polymer material, a rope material, or the like.

8. The knee replacement therapy unit of claim 1 wherein the winch comprises a worm gear drive mechanism.

9. The knee replacement therapy unit of claim 1 wherein the winch is attached proximate an edge of the base board.

10. The knee replacement therapy unit of claim 1 further comprising a cuff for attachment to the cable and a body part of a user.

11. The knee replacement therapy unit of claim 1 wherein the feed mechanism comprises a roller for redirecting movement of the cable.

12. The knee replacement therapy unit of claim 1 wherein the feed mechanism comprises a pair of horizontally-oriented and/or vertically-oriented rollers for redirecting movement of the cable.

13. The knee replacement therapy unit of claim 1 wherein the base board has at least one opening for retaining the rear base board clip plate.

14. The knee replacement therapy unit of claim 13 wherein the at least one opening is an elongated opening extending in a direction perpendicular to the edge of the base board with respect to which the rear base board clip plate extends in parallel.

15. A knee replacement therapy kit, the kit comprising:
a knee replacement therapy unit;
a cable for connection with the knee replacement therapy unit;
a slider puck; and
a cuff for connection with an end of the cable
wherein the knee replacement therapy unit comprises:
a base board configured to be attached with a chair;
a winch having a crank, the winch attached to the base board and configured to wind the cable thereon; and
a feed mechanism attached to the base board and configured to receive the cable therethrough from the winch,
wherein the base board further comprises a front base board clip plate and a rear base board clip plate, each of the front and rear base board clip plates are on a side of the base board and parallel to an edge of the base board, the front and rear base board clip plates are configured to attach the knee replacement therapy unit to the chair, and
wherein at least one of the front or rear base board clip plate in conjunction with the base board forms a groove therebetween having an opening in the same direction as the edge of the base board to which the front or rear base board clip plate is attached.

16. A method of using a knee replacement therapy unit, the method comprising:
attaching a knee replacement therapy unit to a chair, wherein the knee replacement therapy unit has a winch, and
wherein the knee replacement therapy unit has a feed mechanism attached to the base board, configured to receive the cable therethrough and guide the cable in a direction substantially perpendicular to an edge of the knee replacement therapy unit,
wherein the base board further comprises a front base board clip plate and a rear base board clip plate, each of the front and rear base board clip plates are on a side of the base board and parallel to an edge of the base board, the front and rear base board clip plates are configured to attach the knee replacement therapy unit to the chair, and wherein at least one of the front or rear base board clip plate in conjunction with the base board forms a groove therebetween having an opening in the same direction as the edge of the base board to which the front or rear base board clip plate is attached;

connecting one end of a cable to the winch of the knee replacement therapy unit;

connecting the other end of the cable to a portion of a person; and manipulating the winch to retract the cable onto the winch and thereby move the portion of the person toward the chair.

\* \* \* \* \*